United States Patent [19]

McShane

[11] Patent Number: 5,228,342
[45] Date of Patent: Jul. 20, 1993

[54] ULTRASONIC POSITION SENSOR AND METHOD

[75] Inventor: James L. McShane, Churchill Boro, Pa.

[73] Assignee: Westinghouse Electric Corp., Pittsburgh, Pa.

[21] Appl. No.: 736,360

[22] Filed: Jul. 26, 1991

[51] Int. Cl.⁵ .................................... G01N 29/00
[52] U.S. Cl. ............................. 73/597; 73/168
[58] Field of Search ............... 73/572, 597, 627, 629, 73/168; 137/554; 367/99; 376/245, 252

[56] References Cited

U.S. PATENT DOCUMENTS

| | | | |
|---|---|---|---|
| 4,777,979 | 10/1988 | Twerdochlib | 137/554 |
| 4,920,802 | 5/1990 | McMullin et al. | 73/597 |
| 4,977,778 | 12/1990 | Nafziger et al. | 73/168 |
| 5,008,841 | 4/1991 | McElroy | 376/245 |

Primary Examiner—Tom Noland
Assistant Examiner—Rose M. Finley
Attorney, Agent, or Firm—M. G. Panian

[57] ABSTRACT

An ultrasonic position sensing apparatus for detecting open, closed and intermediate positions of a valve element movably mounted in a valve housing includes an ultrasonic target fixedly attached to the valve and having an echo surface which provides a travel time difference for a returning echo, depending on the position of the valve element. An ultrasonic transducer coupled to an outer surface of the valve housing transmits an ultrasonic pulse towards the target thereby generating the echo by striking the target; a monitor means connected to the ultrasonic transducer correlates valve position to the travel time of the returning echo.

15 Claims, 5 Drawing Sheets

VALVE CLOSED

TIME SCALE: 20 µs/div

VALVE FULLY OPEN

TIME SCALE: 20 µs/div

ULTRASONIC POSITION SENSOR AND METHOD

BACKGROUND OF THE INVENTION

1. Field of the Invention

The present invention relates generally to the field of position detection and, more specifically, to an ultrasonic method and apparatus for detecting position of, for example, the movable internal parts of a check valve.

2. Description of the Related Art

Ultrasonic techniques have been used to effect non-destructive testing for part defects or fractures and to effect distance measurement and object detection.

In the nuclear industry, a great deal of attention is directed towards non-intrusive testing and on-line monitoring of, for example, check valves in nuclear power plants. Because these valves, those simple in function, are critical to safe plant operation, they are subject to Nuclear Regulatory Commission (NRC) specified periodic inspections that often require time consuming and expensive partial disassembly.

With particular reference to check valves (which are non-motorized), it is also desirable to not only detect an open (i.e., fully open) or closed position, but also various positions between open and closed positions, as well as the nature of valve element motion. A fluttering motion, for example, could indicate a condition causing excessive wear. Although completely non-intrusive monitoring of unmodified installed valves is desired, methods that require some modification are acceptable, particularly if monitoring capability is greatly enhanced. An example is a magnetic technique, whereby a permanent magnet is mounted on the disk assembly of a check valve and changes in the magnetic field are sensed externally. The fact that a linear change in field cannot be produced and magnetic techniques may not be applicable at all for carbon steel valves are limitations of these techniques. Also, the choice of materials for the modification is limited by the need for permanent magnetism.

While ultrasonic techniques have been employed for check valve inspection and testing, certain problems make their use difficult in this application. For example, valve bodies have contours which limit the possible acoustic path directions, and surface finish may not be adequate for good acoustic coupling. Differences among valves of various manufacturers exacerbate the problem.

While general principles of ultrasonic testing are disclosed in U.S. Pat. Nos. 4,069,433 and 3,925,692, a continuing need exists for an improved ultrasonic testing technique and apparatus for determining valve element position.

SUMMARY OF THE INVENTION

An object of the present invention is to provide an ultrasonic position sensing apparatus and method which is capable of non-intrusive position sensing of a valve element to detect closed and open positions, positions therebetween, and the nature of motions.

Another object of the present invention is to provide an ultrasonic position sensing apparatus and method which requires a minimal amount of modification to an exiting valve structure.

These and other objects of the invention are met by providing an ultrasonic position sensing apparatus for detecting open, closed and intermediate positions and motions of a valve element movably mounted in a valve housing, the apparatus including an ultrasonic target fixedly connected to the valve element or corresponding mounting structure such as a hinge, so that the target is movable with the valve element, and having an echo surface which provides a travel time difference for a returning echo, an ultrasonic transducer on an outer surface of the valve housing and transmitting an ultrasonic wave towards the target, thereby generating the echo by striking the target, and a monitor connected to the ultrasonic transducer for correlating valve position to the travel time of the returning echo.

Preferably, the target presents a flat surface perpendicular to the path of the ultrasonic wave at specific positions of the valve element, with the distance to a flat surface from the ultrasonic transducer being different for different valve element positions. Preferred to a greater extent is a target having a curved surface, with a line tangent to the curve being perpendicular to the path of the ultrasonic wave, and with the target surface changing distance to the transducer with changes in valve element position.

These and other features and advantages of the present invention will become more apparent with reference to the following detailed description and drawings.

DETAILED DESCRIPTION OF THE PREFERRED EMBODIMENTS

In the following description, reference is made to a specific type of valve, known as a swing check valve. It should be understood that the invention can be used to monitor position or movement of movable parts in other types of valves using the same principles of the present invention.

Figure 1:
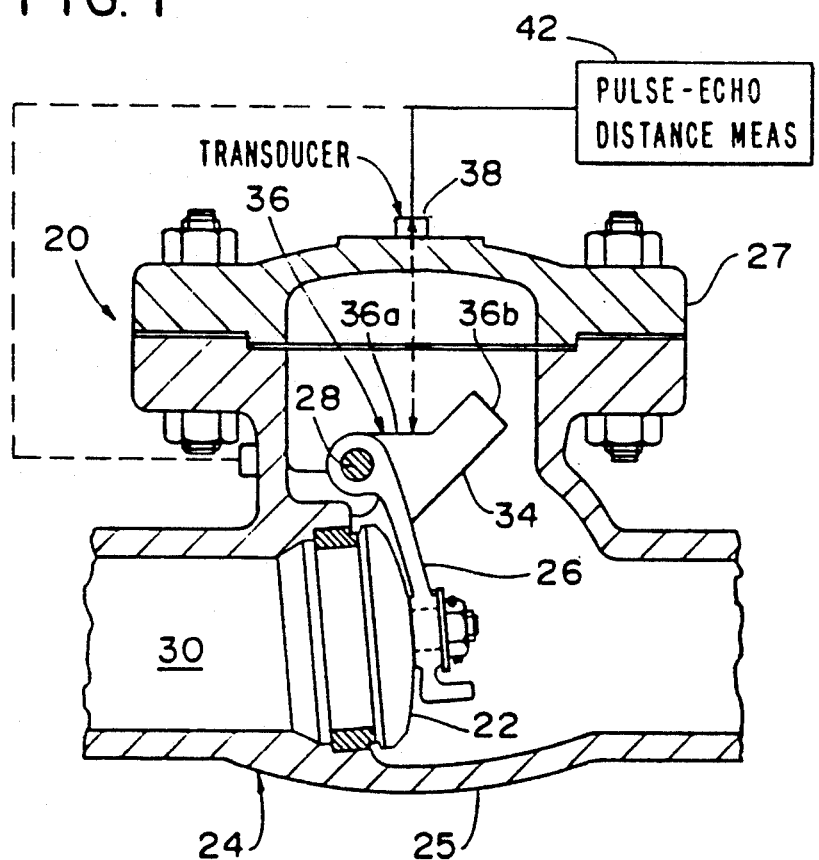
FIG. 1 is a cross-sectional view showing a first embodiment of the present invention, with a valve element in a closed position.
Figure 2:
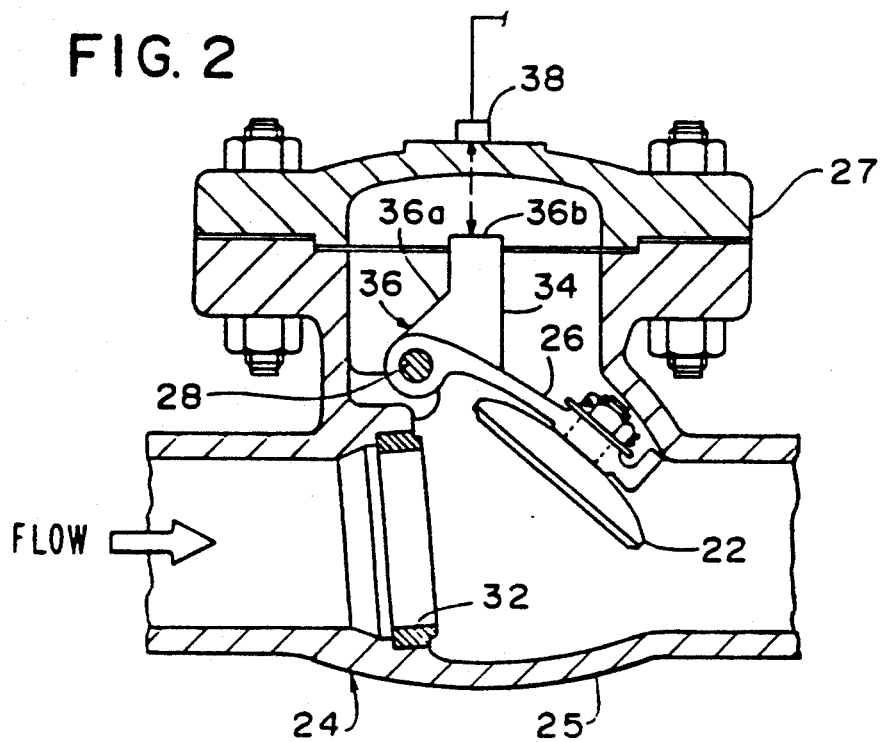
FIG. 2 is a cross-sectional view similar to FIG. 1, except that the valve element is shown in the open position.

Referring now to FIGS. 1 and 2, an ultrasonic position sensing apparatus according to the present invention installed on a swing check valve assembly is generally referred to by the numeral 20 and is used to detect open and closed positions of a valve element 22 movably mounted in a valve housing 24 which includes a body 25 and a bolted on cover 27. In the illustrated embodiment, the position sensing apparatus 20 senses valve element position in a check valve and is used, for example, in the nuclear industry for non-intrusive testing and on-line monitoring of check valves in nuclear power plants. The valve element 22 is pivotally mounted on a hinge 26 which pivots about a pivot pin 28. Under normal conditions, flow of fluid through the housing passageway 30 is from left to right in FIGS. 1 and 2 so that, as shown in FIG. 2, fluid flow induces the valve element to pivot upwardly in a counter-clockwise fashion away from its corresponding valve seat 32.

The valve housing 24 is disposed in a fluid conduit by conventional means and, in fact, the valve assembly itself is known and commercially available.

Because of the irregular geometry of the valve element 22 and its hinge 26, ultrasonic testing using pulse-echo techniques would tend to be impractical because the echo would not be easily propagated along the path of the transmitted wave.

According to the present invention, an ultrasonic target 34 is fixedly attached to the hinge 26 of the valve element 22. The target 34 may be integrally formed with the hinge 26, or may be bolted, riveted, welded, brazed, bonded, etc., to the valve hinge and/or element as an add-on feature; as a retrofit item, it may be necessary, for example, to machine a flat surface on the hinge or valve element in order to attach the target.

The target 34 preferably has an echo surface 36 which has two portions 36a and 36b. These surfaces are shaped to be perpendicularly oriented to the path of an acoustic wave emanating from a transducer 38. As shown in FIG. 1, the transducer is mounted on an outside surface of the cover 27 of the valve housing 24. The transducer 38 could be mounted in other positions on the housing as shown in phantom lines in FIG. 1, so long as a flat target surface is provided perpendicular to the wave when the valve element is in a specific significant position. In the closed position of FIG. 1, the acoustic wave strikes the echo surface portion 36a and produces an echo having a specific travel time. In the open position of FIG. 2, the echo surface portion 36b is positioned in the path of the acoustic wave and produces an echo having a different travel time than the one produced in FIG. 1. The differences in position indication are attributable to the travel time difference for the returning echo. It can be seen from the figures that the distance between the echo surface portion 36a and the transducer, and echo surface portion 36b and the transducer is different, with the echo surface portion 36b being closer to the transducer 38. The target is thus used to enhance the ultrasonic echo and control its direction. The position of the valve element 22 can thus be correlated to travel time of the ultrasonic wave, the "travel time" being understood to mean the total time for the transmitted wave and the echo or reflected wave to be transmitted and received.

If it is only necessary to detect one position, such as either open or closed, the target would need to have only one surface which, when moved to a position in the path of the wave, would signal the open or closed position.

The target 34 is a plate-like element which can be added on by conventional fasteners. The ultrasonic target presents a horizontal surface to a vertically propagating ultrasonic pulse only when the valve is fully closed or fully open. As illustrated, the respective horizontal surfaces are separated vertically, thus providing a travel time difference for the returning echo. The echo signal can be displayed on an oscilloscope or otherwise processed by a pulse-echo distance measuring device 42. Additional surfaces could be provided so that various intermediate positions of the valve element could also be detected.

Figure 3:
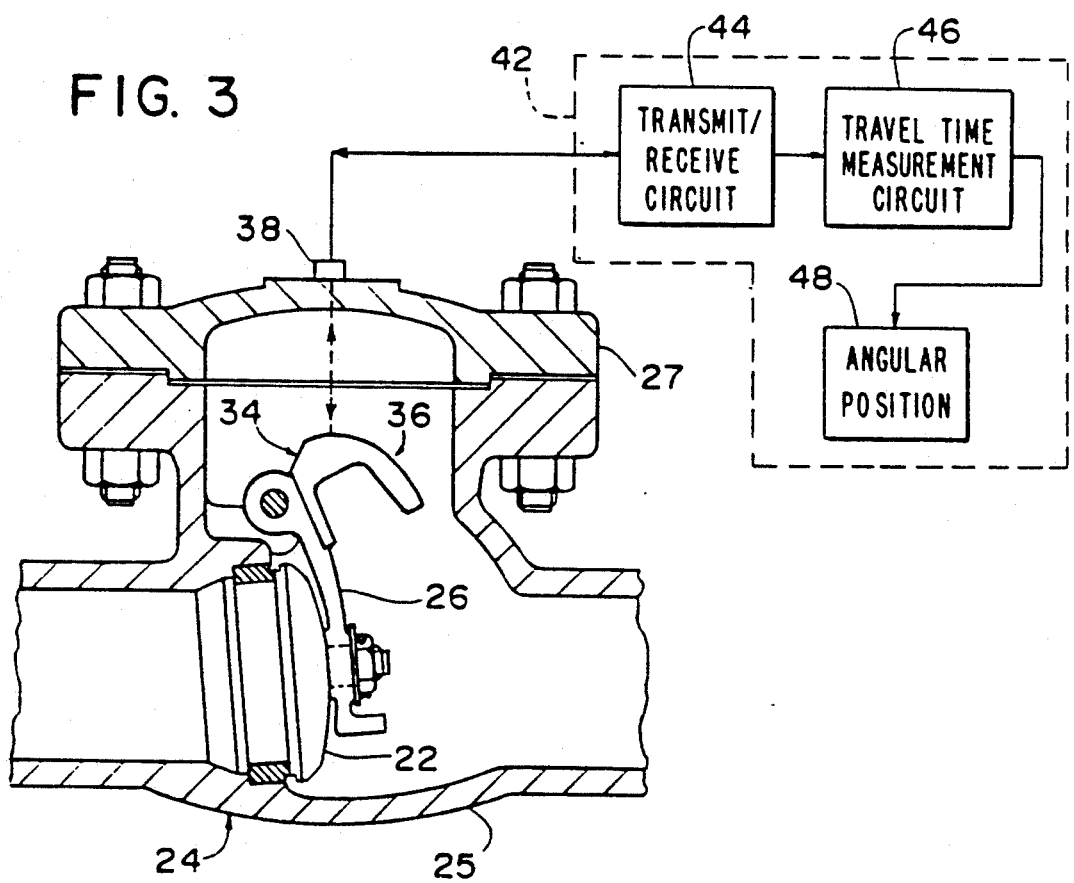
FIG. 3 is a cross sectional view, partly schematic, showing another embodiment of the present invention, with the valve element shown in the closed position.
Figure 4:
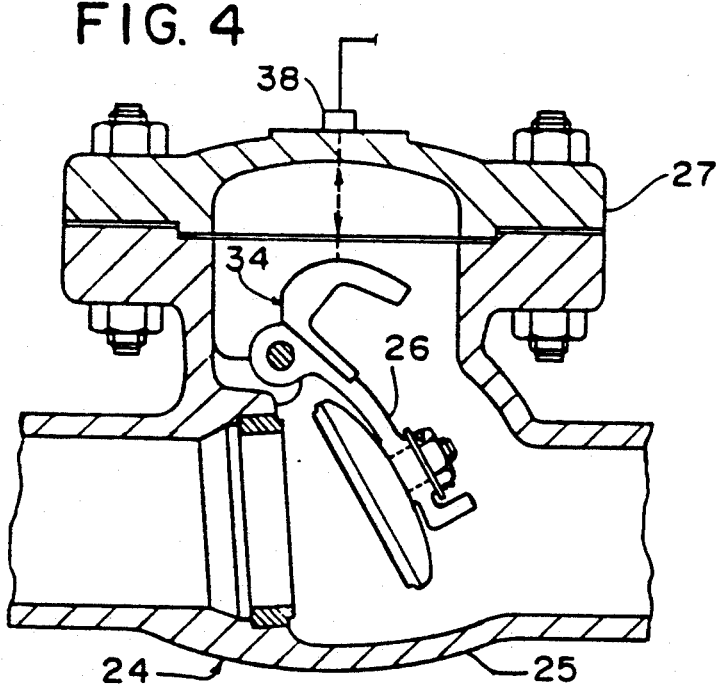
FIG. 4 is a sectional view similar to FIG. 3, showing the valve element in an intermediate position.
Figure 5:
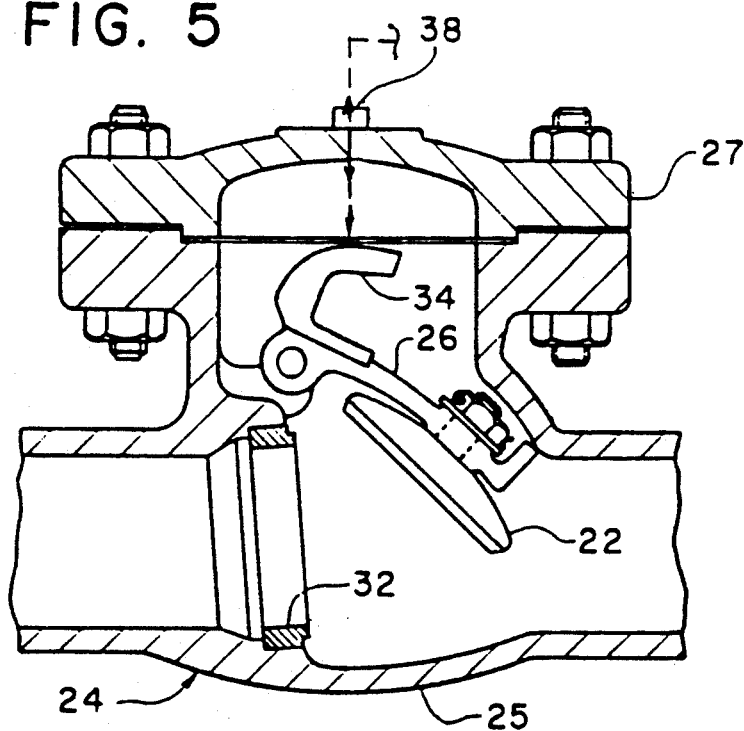
FIG. 5 is a cross sectional view of the valve assembly of FIG. 3, with the valve element in the open position.

In a preferred embodiment, illustrated in FIGS. 3-5, the target 34 has a continuously curved echo surface 36 so that a perpendicular surface is always presented to the ultrasonic wave. Also shown in FIG. 3 is a more detailed representation of the measuring device 42, which includes a transmit/receive circuit 44 (of conventional construction), and a travel time measurement circuit 46. An angular position display 48 can be used to indicate the angular position of the valve element, correlated to a closed, open or intermediate position. FIG. 3 illustrates the valve element in the closed position, while FIG. 4 illustrates the valve element in an intermediate position, and FIG. 5 illustrates the valve element in an open position.

Figure 6:
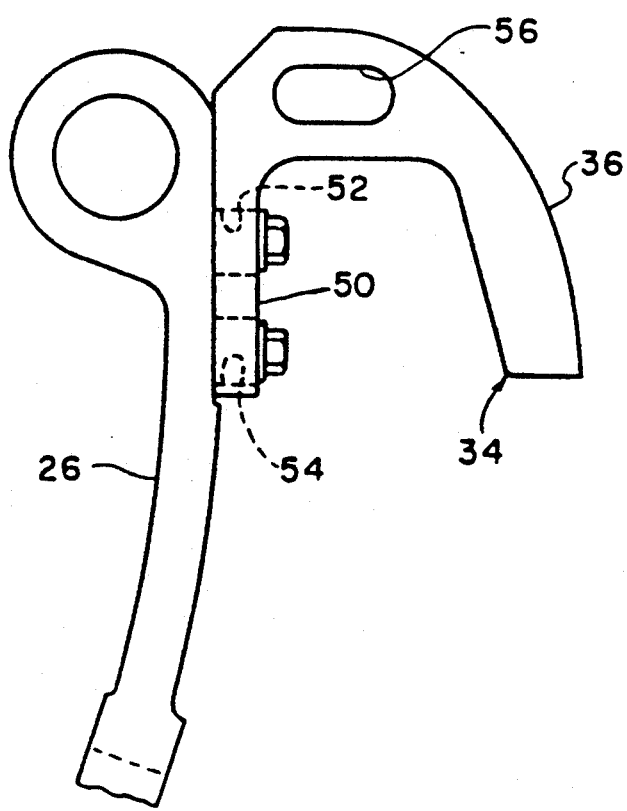
FIG. 6 is a side elevational view of a target according to the present invention.
Figure 7:
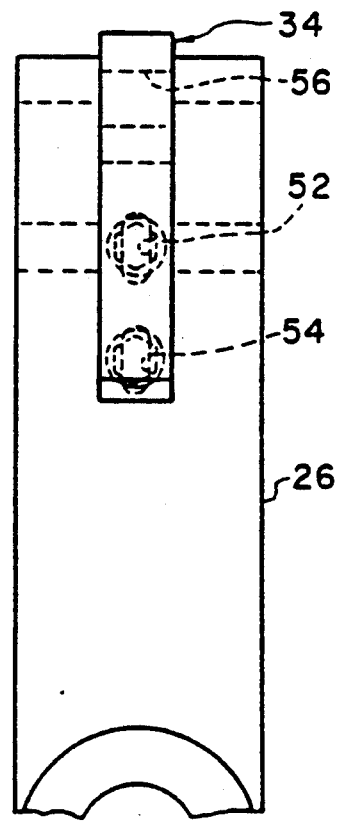
FIG. 7 is an end view of the target of FIG. 6.

According to this preferred embodiment of the invention, the echo surface of the target is formed as a continuously curved surface so as to present a perpendicular surface to the ultrasonic wave while changing its vertical position as the hinge rotates. This provides a continuous position measurement in terms of ultrasonic travel time. An example of this type of target is illustrated in FIGS. 6 and 7. As illustrated, the echo surface 36 is a continuous curve. A mounting arm 50 is provided with a pair of mounting holes 52 and 54 which can be used to attach the target 34 to the hinge 26 of the valve element 22.

Figure 8:
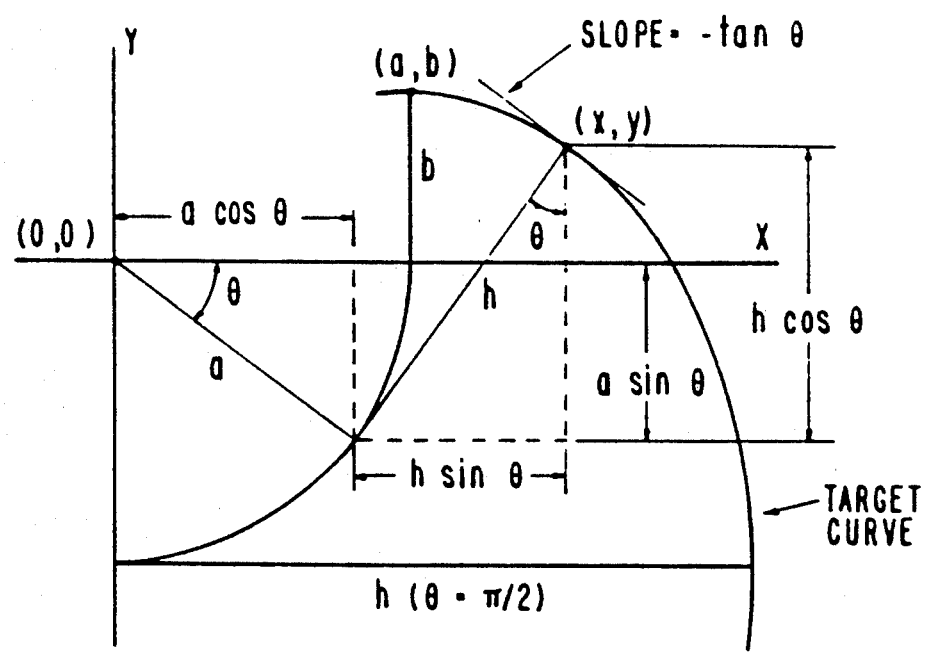
FIG. 8 is a graph showing formation of a target curve according to the present invention.

In order to define the shape of the echo surface for fabricating the target, mathematical expressions for the curve were derived. In the following discussion, it is assumed that the physical acoustic path is vertical, as in FIGS. 3 to 5, but the path could have any orientation, so long as the propagating wave is perpendicular to the target. FIG. 8 shows the geometry used in the derivation. The vertical line spaced a distance a horizontally from the origin (which is the hinge pin axis) represents the true vertical in the position for which $\Theta=0$, where $\Theta$ is the angle of hinge rotation. The reflecting surface is a distance b above the origin. For purposes of derivation, the coordinate system is fixed with respect to the target. Thus, instead of the drawn target rotating, the vertical acoustic path is rotated, staying the same distance from the origin and therefore being tangential to a circle centered on the origin. The vertical height above the origin for an angle $\Theta$ (positive in the direction shown) is represented by the distance h. Therefore, b is the value of $\Theta$ for $\Theta=0$. From the diagram in FIG. 8, $x = a \cos \Theta + h \sin \Theta$. Also, $y = -a \sin \Theta + h \cos \Theta$. For the curve tangent line to be perpendicular to the acoustic path at point (x, y), $dy/dx = -\tan \Theta$. Substituting initial conditions and solving these equations for h yields the following: $h = a\Theta + b$, where $\Theta$ is expressed in radians. Differentiating with respect to $\Theta$ yields $dh/d\Theta = a$. Thus, the change in acoustic path length is linear with respect to rotation angle. Substituting for h from the equation $h = a\Theta + b$ into the equations for x and y gives the following: $x = a \cos \Theta + a\Theta \sin \Theta + b \sin \Theta$, and $y = -a \sin \Theta + a\Theta \cos \Theta + b \cos \Theta$. These equations define the curve since both x and y are functions of $\Theta$. As the extensions of the target curve in FIG. 8 indicate, $\Theta$ values are not limited to the range between 0 and $\pi/2$ radians (90°). For the typical check valve application, however, this range is more than adequate.

For experimental verification, a was chosen to position the acoustic path in the center of the test valves top opening and b was chosen to place the reflecting surface above the hinge hub at the $\Theta=0$ position. A milling machine can then be used to create the echo surface by programming into a numeric control machine tables of x and y values calculated by incrementing $\Theta$ in the above equations. It should be noted that in the target illustrated in FIG. 6, an opening 56, as well as the large U-shaped cutout, were provided partially to reduce weight, but further weight reduction, for example, by thinning portions of the target, is possible and desirable to minimize effects on valve operation. The U-shaped cut-out in FIG. 6 also serves to form the mounting arm 50.

The target may be machined from brass material and can be attached to the hinge by two screws, although other materials (e.g., metals, ceramics, or plastics) and means of attachment could be used. As an example, with the target mounted on the hinge, the target may be in a position where $\Theta \neq 0$ when the valve is closed. For the target of FIGS. 6 and 7, $\Theta$ was 23° when the valve was closed, with the rotational travel to the fully opened position being only about 50°. Because the change in target surface position is linear with rotation angle, any part of the target curve provides the same measurement sensitivity. The transducer 38 can be of any conventional type, such as a 5 MHz nondestructive testing transducer and can be coupled using conventional couplants for temporary installation.

For permanent installation and/or high temperature operation, the transducer itself is preferably dry-coupled, by using techniques similar to those described in U.S. Pat. Nos. 3,925,692 and 4,069,433.

Figure 9:
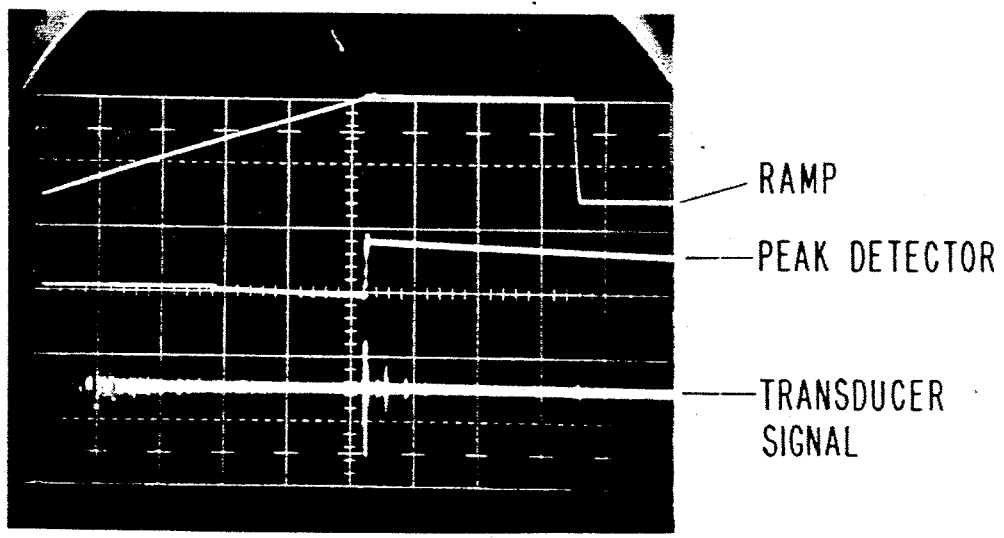
FIGS. 9 and 10 are charts generated by an oscilloscope showing transducer signals and related waveforms for valve closed and valve open positions, respectively.
Figure 10:
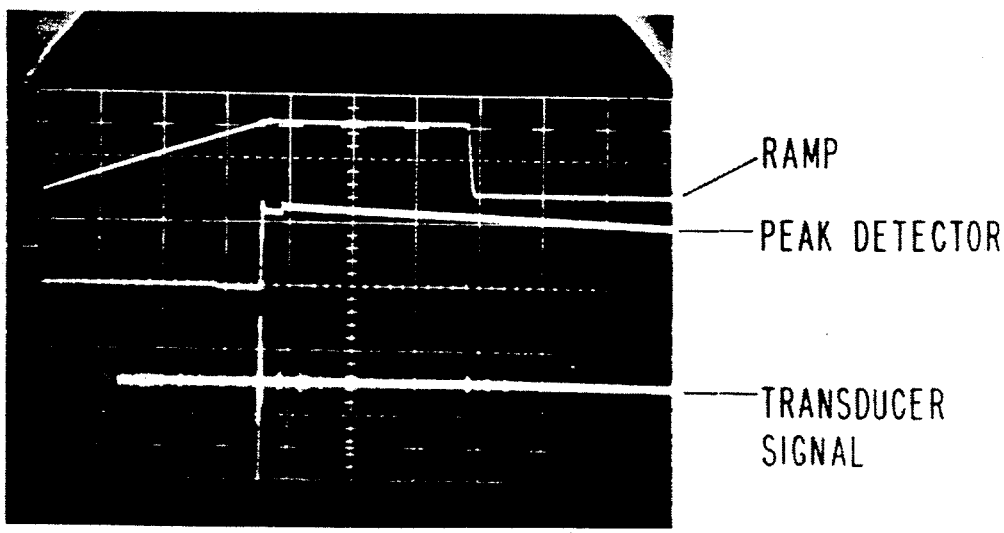

FIGS. 9 and 10 show three waveforms, the amplified echo (transducer signal), a peak-detected version of the echo, and the ramp used to develop the DC output voltage, for the closed and fully opened positions. These figures are based on oscilloscope displays, and demonstrate one technique for correlation of echo travel time to valve element position. The ramp starts with the occurrence of the transmit pulse and ends with the arrival of the echo. A peak hold circuit generates a DC voltage equal to ramp height. Note that the DC voltage, V, would decrease from a fixed value, $V_{closed}$, corresponding to the closed position, as the valve opens. If an angle $\phi$ is defined as increasing from zero as the valve opens, the relationship, $V - V_{closed} = K\phi$, holds, where $K = dV/d\phi$, a constant by virtue of the target's linear effect. Since K is negative in this case, a positive output voltage proportional to angle is given by $V_{out} = V_{closed} - V$, since $V_{closed} - V = -K\phi$. In practice, the measured DC voltage would simply be subtracted from a voltage source adjusted to be equal to $V_{closed}$. Chart recordings of the output voltage as valve element moved were essentially identical with recordings of voltage from a potentiometer driven by a mechanical linkage from the element. Also, as indicated by FIGS. 9 and 10, the echo magnitude changed very little over the full range.

The present invention provides a method and apparatus for non-intrusively measuring the position of a check valve element. Knowledge of the position, and hence motion, is the best indicator of correct valve operation or problems. The demonstrated good performance of the present invention could overcome possible objections to the need to modify valves. Many variations of the present invention can be envisioned. In particular, the use of practically any transducer type, size, frequency, and location can be envisioned, with any means of coupling. As an example, referring to FIG. 1, a transducer 38' could be located on the side of the housing 24 to produce a horizontally propagating wave. In this case, the target could be modified to present a vertically oriented surface, or the hinge itself could be machined to include various flat surfaces or a continuously curved surface around the pin 28. Also, the target reflecting surface could be rounded in a transverse direction or roughened to account for tilting in a transverse plane that could occur, for example, if the hinge pin was worn. The specular echo from a very smooth, non-rounded surface could be deflected off line by a transverse tilt of the target.

The present invention is not limited to the type of valve described herein. Any means of mounting the target or making it integral with the hinge or of attachment of the target to the valve element or other moving part could be envisioned. Moreover, grooving or roughening of the hinge or attachment of other targets, for example, a spherical or cylindrical protrusion, for improved ultrasonic echoes but not necessarily a linear response over a wide range of positions can also be employed.

Another variation of the present invention would be to provide a target shape which changes transverse acoustic path length with rotation, by having, for example, a variable thickness. "Transverse" means that the acoustic path is parallel to the axis of rotation. Additionally, holes or protrusions that would indicate discrete positions by admitting or interrupting an ultrasonic beam could be provided on the target.

While it may be necessary to machine the outer surface of the cover 40 to provide a smooth attachment surface for the transducer, the use of special covers having material or shape more favorable for ultrasonics may be employed.

While the target was described as being machined from brass and other ordinary materials, the use of a permanently magnetic material for the target, or attaching a magnet to the target, may be desirable for providing a combined ultrasonic/magnetic sensing capability, particularly for two-phase fluid conditions which may occur.

The transducer itself may be permanently affixed to the valve housing or may be detachably coupled for inspection purposes only. Dry-coupling could be used to permanently mount the transducer for repeated valve inspections or continuous monitoring. Alternatively, a suitable coupling surface and/or mounting hardware could facilitate repeated transducer installations.

The present invention is particularly appropriate for inclusion in the design of new valves, thus obviating the need for opening a valve and modifying surfaces in order to attach the target. Also, the present invention can be used to measure rotation angle for any purpose, or could determine angular position of a movable acoustic source using a fixed target. The curved surface may also have a spiral shape so that $\Theta$ covers a wider range. A lateral offset could be used to avoid blocking the beam to inside portions of the curve. This embodiment would be more applicable to non-valve cases.

Numerous modifications and adaptations of the present invention will be apparent to those so skilled in the art and thus, it is intended by the following claims to cover all such modifications and adaptations which fall within the true spirit and scope of the invention.

What is claimed is:

1. An ultrasonic position sensing apparatus for detecting open, closed and intermediate positions of a valve element movably mounted in a valve housing comprising:
   an ultrasonic target movable with the valve element and having an echo surface which provides a travel time difference for a returning echo, depending on the position of the valve element, at least one portion of the echo surface corresponding to a specific position of the valve element;
   an ultrasonic transducer connected to an outer surface of the valve housing and outputting an ultrasonic pulse towards the target, thereby generating the echo by striking the target; and
   a monitor means coupled to the ultrasonic transducer for correlating valve position to the travel time of the returning echo.

2. An ultrasonic position sensing apparatus as recited in claim 1, wherein the monitor means comprises a transmit/receive circuit connected to the transducer, a travel time measurement circuit connected to the transmit/receive circuit, and a display for displaying valve element position based on the measured travel time of the echo.

3. An ultrasonic position sensing apparatus as recited in claim 1, wherein the ultrasonic target has a curved echo surface, wherein points along the curved echo surface correspond to open, closed, or intermediate positions of the valve element, thereby providing a continuous indication of valve element position and motion.

4. An ultrasonic position sensing apparatus as recited in claim 3, wherein the curved echo surface has a point (x,y) thereon defined in a rectangular coordinate system fixed with respect to the target by the equations $$x = a \cos \Theta + a\Theta \sin \Theta + b \sin \Theta, \text{ and}$$

$$y = -a \sin \Theta + a\Theta \cos \Theta + b \cos \Theta,$$

wherein (a,b) is the point on the curve corresponding to $\Theta = 0$; 0 is an angle between the x axis and a line through the origin, increasing in a clockwise direction;
   h is the distance from a point (a cos $\Theta$, a sin $\Theta$) on a circle of radius a around the origin to the point (x,y), the line through these two points being tangent to said circle and also being colinear with the acoustic path, and the origin, point (0,0), is the axis of rotation of the target.

5. An ultrasonic position sensing apparatus as recited in claim 1, wherein the ultrasonic transducer is dry-coupled to the outer surface of the valve housing.

6. An ultrasonic position sensing method for detecting open, closed and intermediate positions of a valve element movably mounted in a valve housing comprising:
   providing an ultrasonic target on the valve element, the valve element having an echo surface which provides a travel time difference for a returning echo depending on a position of the valve element;
   defining a portion of the echo surface as corresponding to a particular position of the valve element;
   coupling an ultrasonic transducer to an outer surface of the valve housing and outputting an ultrasonic pulse towards the target, the pulse thereby generating the echo by striking the target; and
   monitoring the echo of the ultrasonic transducer with monitoring means and correlating a valve element position to a magnitude of the returning echo.

7. An ultrasonic position sensing method as recited in claim 6, wherein the monitor means comprises a transmit/receive circuit connected to the transducer, a travel time measurement circuit connected to the transmit/receive circuit, and a display for displaying valve element position based on the measured travel time of the echo.

8. An ultrasonic position sensing method as recited in claim 7, wherein the ultrasonic target has a curved echo surface, wherein points along the curved echo surface correspond to a closed, open, or intermediate positions of the valve element, thereby providing a continuous indication of valve element position and motion.

9. An ultrasonic position sensing method as recited in claim 8, wherein the curved echo surface has a point (x,y) thereon defined by the equations $$x = a \cos \Theta + a\Theta \sin \Theta + b \sin \Theta, \text{ and}$$

$$y = -a \sin \Theta + a\Theta \cos \Theta + b \cos \Theta,$$

wherein (a,b) is the point on the curve corresponding to $\Theta = 0$; 0 is an angle between the x axis and a line through the origin, increasing in a clockwise direction;
   h is the distance from a point (a cos $\Theta$, a sin $\Theta$) on a circle of radius a around the origin to the point (x,y), the line through these two points being tangent to said circle and also being colinear with the acoustic path, and the origin, point (0,0), is the axis of rotation of the target.

10. An ultrasonic position sensing method as recited in claim 9, wherein the ultrasonic transducer is dry-coupled to the outer surface of the valve housing.

11. An ultrasonic position sensing apparatus as recited in claim 1, wherein the ultrasonic target is comprised of a permanently magnetic material.

12. An ultrasonic position sensing apparatus for detecting opened, closed and intermediate positions of a valve element movably mounted in a valve housing comprising:
   an ultrasonic target movable with the valve element and having a curved echo surface which provides a travel time difference for a returning echo, wherein points along the curved echo surface correspond to open, closed, or intermediate positions of the valve element;
   an ultrasonic transducer connected to an outer surface of the valve housing and outputting an ultrasonic pulse towards the target, thereby generating the echo by striking the target; and
   a monitor means coupled to the ultrasonic transducer for correlating valve position to the travel time of the returning echo.

13. An ultrasonic position sensing apparatus as recited in claim 12, wherein the curved echo surface has a point (x,y) thereon defined by the equations $$x = a \cos \Theta + a\Theta \sin \Theta + b \sin \Theta, \text{ and}$$

$$y = -a \sin \Theta + a\Theta \cos \Theta + b \cos \Theta,$$

wherein (a,b) is the point on the curve corresponding to $\Theta = 0$; $\Theta$ is an angle between the x axis and a line through the origin increasing in a clockwise direction;

h is the distance from a point (a cos Θ, a sin Θ) on a circle of radius a around the origin to the point (x,y), the line through these two points being tangent to said circle and also being collinear with the acoustic path, and the origin, point (0,0) is the axis of rotation of the target.

14. An ultrasonic position sensing apparatus as recited in claim 13, wherein the ultrasonic transducer is drycoupled to the outer surface of the valve housing.

15. An ultrasonic position sensing apparatus as recited in claim 12, wherein the ultrasonic target is comprised of a permanently magnetic material.

* * * * *

UNITED STATES PATENT AND TRADEMARK OFFICE
CERTIFICATE OF CORRECTION

PATENT NO. : 5,228,342

DATED : July 20, 1993

INVENTOR(S) : James L. McShane

It is certified that error appears in the above-identified patent and that said Letters Patent is hereby corrected as shown below:

Claim 4, line 8 (column 7, line 43), change " θ=θ; 0 " to -- θ=0; θ --;

Claim 9, line 7 (column 8, line 27), change " θ=0; 0 " to -- θ=0; θ --;

Signed and Sealed this

Thirteenth Day of December, 1994

Attest:

BRUCE LEHMAN

*Attesting Officer*      *Commissioner of Patents and Trademarks*